United States Patent [19]
Portnoff

[11] 4,398,909
[45] Aug. 16, 1983

[54] UNIT DOSE APPLICATOR

[76] Inventor: Joel B. Portnoff, 76 Gregory Pl., Richboro, Pa. 18954

[21] Appl. No.: 336,223

[22] Filed: Dec. 31, 1981

[51] Int. Cl.³ ............................................. A61M 1/00
[52] U.S. Cl. ................................................... 604/295
[58] Field of Search ...................... 128/233, 232, 261; 604/294, 295, 298, 289, 19; 5/451

[56] References Cited

U.S. PATENT DOCUMENTS

| 565,480 | 8/1896 | Maloney | 128/233 |
| 1,644,606 | 10/1927 | Pelphrey | 128/232 X |
| 1,960,858 | 5/1934 | Strauch | 128/232 X |
| 2,965,255 | 12/1960 | Gerarde | 128/233 X |

FOREIGN PATENT DOCUMENTS

| 355895 | 9/1961 | Switzerland | 128/233 |
| 22299 | 2/1910 | United Kingdom | 128/233 |

Primary Examiner—John D. Yasko
Attorney, Agent, or Firm—Edmunde D. Riedl; Mario A. Monaco; Michael C. Sudol, Jr.

[57] ABSTRACT

A unit dose applicator for liquid ophthalmic medicaments in solution or suspension has an elongated housing for the medicament; at one end of the housing there is an opening for at least partially emptying the contents of the housing; at the other end of the housing is a second opening; and the second opening is capped by a diaphragm-like seal having a sufficient displacement potential to exude only 1 to 4 drops of the medicament.

1 Claim, 2 Drawing Figures

U.S. Patent  Aug. 16, 1983  4,398,909

UNIT DOSE APPLICATOR

DISCLOSURE OF THE INVENTION

This invention relates to a unit dosage delivery of ophthalmic medicament. More particularly it relates to a unit dosage delivery device for delivery of 1-2 drops to each eye of a patient. Most especially, this invention relates to means for delivery of measured quantities of medicament to the eye without the potential of having the medicament stream from the delivery source and flood the eye with excess medicament.

In meeting the objectives of this invention, a unit does applicator comprising an elongated housing for a liquid ophthalmic medicament having at the distal end an opening for at least partially emptying the contents of the housing; and at the proximal end a second opening capped by a diaphragm-like seal having a sufficient displacement potential to expel only 1 to 4 or 5 drops is provided. In the prior art, eye droppers were available having large bulbous expulsion means. These had the disadvantage of being difficult to control, requiring dexterity of manipulation to expel only a single drop, and the drawback of streaming a large volume of contents in non-drop form thereby flooding the eye with medicament.

Figure 1:
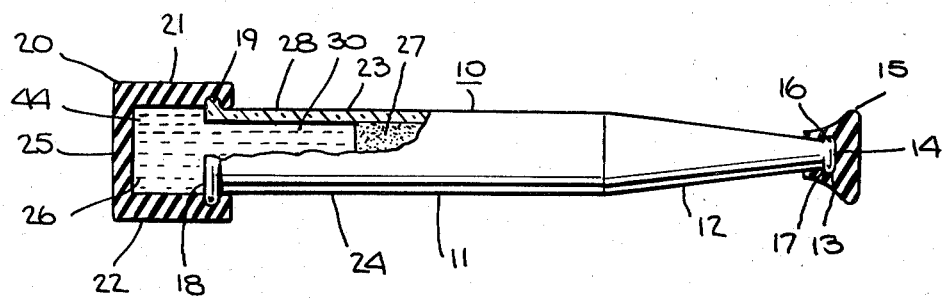
Figure 2:
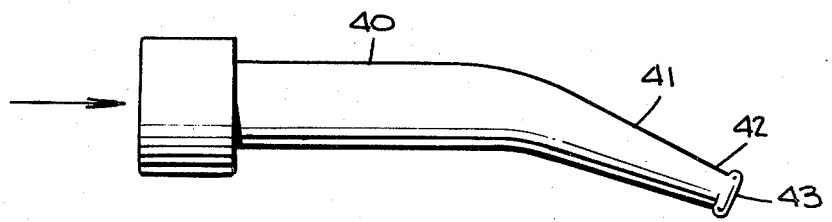

The invention can be best understood by reference to the enclosed drawing in which FIG. 1 is a partially cut-away side view of one embodiment of this invention, and in which FIG. 2 is a side-view of another embodiment of this invention.

Referring to FIG. 1, there is shown the unit dosage delivery device 10 of this invention having an elongated housing 11 having at the distal end a tapered nozzel 12. At the end 13 of nozzel 12 is opening 14 that is capped by a friction fitting cap 15. A rim 16 surrounds opening 14 that cooperates with and frictionally fits into flange 17 of cap 15 to better hold cap 15 over opening 14 until removed.

At the other end of housing 11 is a second opening 18. Surrounding opening 18 is a rim 19 about which is seated expulsion cap 20. This cap 20 comprises sidewalls 21, 22 which are suitably substantially parallel to and preferably co-extensive with the walls 23, 24 of housing 10. At the proximal end of cap 20 and contiguous with sidewalls 23, 24 is diaphragm 25. Between diaphragm 25 and opening 18 of housing 10 and defined by sisewalls 21, 23 is headspace 26. This headspace 26 is sufficient to be equivalent in volume to 1 to 4 or 5 drops of ophthalmic medicament. Diaphragm 25 is sufficiently resilient to flex and upon depression intrude into headspace 26.

Headspace 26 can be fully or partially filled with the contents of housing 10. If partially filled, there remains air space 44 just below diaphragm 25 when the device is positioned for delivery.

In housing 10, there is medicament 27, which is a liquid solution or suspension, of an opthalmically active substance. Since, as shall be apparent, not all the contents of the housing are expelled, to conserve drug and avoid waste, the upper portion 28 of housing 10 can be filled with an impeller fluid 30 comprising inert gel or oil immisicible with medicament 27. The gel can suitably be an aqueous gel of an ether or ester polymer derivative of cellulose such as hydroxypropylcellulose or the like.

Housing 10 is made of any inert non-toxic material that is not attached by the contents on storage. Generally glass is found to be particularly advantageous. Cap 15 and cap 20 are generally an inert resilient material, butyl rubber being most suitable and preferred.

In operation, cap 15 is removed, the distal end 13 is positioned over a patient's eye. The operator then depresses diaphragm 25 by tapping once or gently pressing it so it intrudes into and diminishes headspace 26 to displace a single drop of medicament 27 from opening 14. This can be repeated again for a subsequent two or three drops in either the same or contralateral eye. Generally, the total deliverable capacity of the device is one to five drops although the total volume of housing 10 including medicament 27 and impeller fluid 30 can be in the range of 10 to 40 even 75 drops. A suitable volume is about 10 to 60 times the maximum headspace 26, and most suitably 15 to 40 times.

In another embodiment shown in FIG. 2, there is a housing 40 having a tapered nozzle 41 that is directed angularly away from the longitudinal axis of housing 40. This nozzel terminates at the distal end 42 in opening 43. In other respects the embodiment shown in FIG. 2 is structurally and operationally equivalent to the embodiment of FIG. 1.

I claim:

1. A unit dose applicator for the delivery of an ophthalmic medicament to the eye comprising an elongated housing having a first and second end; at the first end a nozzel having at the distal end thereof an opening, at the opposite end of the housing cap, said cap in sealing engagement with the opening and having sidewalls and an end wall, the sidewalls essentially in parallel alignment with the sidewalls of the housing at proximal end and said end wall spaced from the proximal end of the housing so that the end wall and sidewalls define a headspace, and the end wall deformable so that upon deformation inward toward the proximal end, said end wall intrudes into the headspace to displace from 1 to 6 drops from the distal end of the housing, and wherein the housing contains a medicament, said medicament adjacent the opening at the distal end and intermediate the medicament and opening at the proximal end of the housing is an impeller fluid that is inert to and immicible with the medicament.

* * * * *